United States Patent
Brenner

(10) Patent No.: US 6,497,681 B1
(45) Date of Patent: Dec. 24, 2002

(54) DEVICE AND METHOD FOR HOLDING AND MAINTAINING THE POSITION OF A MEDICAL DEVICE SUCH AS A CARDIAC PACING LEAD OR OTHER INTRAVASCULAR INSTRUMENT AND FOR FACILITATING REMOVAL OF A PEELABLE OR SPLITTABLE INTRODUCER SHEATH

(75) Inventor: Laurence D. Brenner, Exton, PA (US)

(73) Assignee: Thomas Medical Products, Inc., Malvern, PA (US)

( * ) Notice: Subject to any disclaimer, the term of this patent is extended or adjusted under 35 U.S.C. 154(b) by 321 days.

(21) Appl. No.: 09/586,016

(22) Filed: Jun. 2, 2000

(51) Int. Cl.$^7$ ............................................. A61M 5/178
(52) U.S. Cl. .................. 604/164.05; 604/160; 604/161; 604/524
(58) Field of Search ............................ 604/164.05, 524, 604/95, 264, 526, 527, 528, 523, 96.01, 101.01, 101.05; 606/191–197

(56) References Cited

U.S. PATENT DOCUMENTS

| | | |
|---|---|---|
| 3,831,274 A | 8/1974 | Horrocks |
| 3,877,429 A | 4/1975 | Rasumoff |
| 3,898,733 A | 8/1975 | Cormier |
| 3,988,826 A | 11/1976 | Heikkala |
| 4,054,136 A | 10/1977 | von Zeppelin |
| 4,394,828 A | 7/1983 | Garbis et al. |
| 4,434,554 A | 3/1984 | Korbelak |
| 4,489,491 A | 12/1984 | Gregson |
| 4,596,559 A | 6/1986 | Fleischhacker |
| 4,631,059 A | 12/1986 | Wolvek et al. ............... 604/280 |
| 4,687,469 A | 8/1987 | Osypka ........................ 604/161 |
| 4,743,265 A * | 5/1988 | Whitehouse et al. ........ 604/161 |
| 4,840,613 A | 6/1989 | Balbierz ........................ 604/51 |
| 4,921,479 A | 5/1990 | Grayzel ......................... 604/53 |
| 4,983,168 A | 1/1991 | Moorehead ................... 604/161 |
| 4,985,018 A | 1/1991 | Smith |
| 4,997,424 A | 3/1991 | Little |

(List continued on next page.)

FOREIGN PATENT DOCUMENTS

| | | | |
|---|---|---|---|
| EP | 0362462 | 4/1990 | .......... A61M/25/06 |
| EP | 0 391 544 A1 | 10/1990 | |
| EP | 0522735 | 1/1993 | .......... A61M/25/06 |
| EP | 0339812 | 12/1993 | .......... A61M/25/00 |
| EP | 0631793 | 4/1995 | .......... A61M/25/06 |
| EP | 0655257 | 5/1995 | .......... A61M/25/00 |
| EP | 0709108 | 1/1996 | .......... A61M/25/00 |
| WO | WO 97/40880 | 6/1997 | .......... A61M/25/06 |
| WO | WO 99/22804 | 5/1999 | .......... A61M/39/00 |
| WO | WO 99/34849 | 7/1999 | ............ A61M/5/00 |

*Primary Examiner*—Joseph Pelham
*Assistant Examiner*—Vinod D Patel
(74) *Attorney, Agent, or Firm*—Caesar, Rivise, Bernstein, Cohen & Pokotilow, Ltd.

(57) ABSTRACT

A holding device and method of use with a peelable or otherwise splittable introducer sheath or catheter through which a cardiac pacing lead or other elongated flexible instrument extends into the body of a living being. The introducer is arranged to be grasped by a user to pull the introducer in the proximal direction so that can be withdrawn out of the being's body. The holding device comprises a first or "gripper" portion and a second or "splitter" portion. The gripper portion includes at least one gripping member, e.g., a pair of jaws or at least one recessed engagement surface, to grasp or frictionally engage a portion of the periphery of the elongated flexible member to enable the user to hold the pacing lead at a desired position within the being's body. The splitter portion of the holding device is arranged to cause the introducer to separate longitudinally, e.g., the second portion includes a sharp edge portion for engaging the introducer member to split it longitudinally when it is pulled proximally with respect to the holding device as the holding device is held in place with the gripper portion gripping the pacing lead. Once the introducer has separated, e.g., split longitudinally, it can be removed from the pacing lead, leaving the pacing lead in place at the desired position within the being's body.

49 Claims, 7 Drawing Sheets

U.S. PATENT DOCUMENTS

| | | | | |
|---|---|---|---|---|
| 5,024,666 | A | 6/1991 | Pituch | 604/263 |
| D318,733 | S | 7/1991 | Wyzgala | D24/112 |
| D318,734 | S | 7/1991 | Wyzgala | D24/112 |
| 5,098,392 | A | 3/1992 | Fleischhacker et al. | 604/165 |
| 5,125,904 | A | 6/1992 | Lee | 604/164 |
| 5,181,913 | A | 1/1993 | Erlich | 604/263 |
| 5,188,605 | A | 2/1993 | Sleep | |
| 5,188,606 | A | 2/1993 | Maloney et al. | |
| 5,242,426 | A | 9/1993 | Pituch | 604/263 |
| 5,250,033 | A | 10/1993 | Evans et al. | 604/160 |
| 5,261,887 | A | 11/1993 | Walker | |
| 5,312,355 | A | 5/1994 | Lee | 604/160 |
| 5,322,513 | A | 6/1994 | Walker | |
| 5,330,460 | A | 7/1994 | Moss et al. | |
| 5,409,469 | A | 4/1995 | Schaerf | 604/282 |
| 5,415,639 | A | 5/1995 | VandenEinde et al. | 604/283 |
| 5,489,273 | A * | 2/1996 | Whitney et al. | 604/160 |
| 5,613,953 | A | 3/1997 | Pohndorf | 604/165 |
| 5,647,857 | A | 7/1997 | Anderson et al. | 604/264 |
| 5,687,727 | A | 11/1997 | Kraus et al. | |
| 5,713,867 | A | 3/1998 | Morris | 604/164 |
| 5,827,227 | A | 10/1998 | DeLago | 604/104 |
| 5,827,313 | A | 10/1998 | Ream | 606/171 |
| 5,868,755 | A | 2/1999 | Kanner et al. | 606/108 |
| 5,873,858 | A | 2/1999 | Schafer et al. | |
| 5,906,593 | A | 5/1999 | Schafer et al. | |
| 5,951,518 | A | 9/1999 | Licata et al. | 604/161 |
| 6,131,289 | A | 10/2000 | Tarpill | |
| 6,148,521 | A | 11/2000 | Eslambolchi et al. | |
| 6,159,198 | A | 12/2000 | Gardeski et al. | |
| 6,280,433 | B1 * | 8/2001 | McIvor et al. | 604/524 |
| 6,379,346 | B1 * | 4/2002 | McIvor et al. | 604/524 |

* cited by examiner

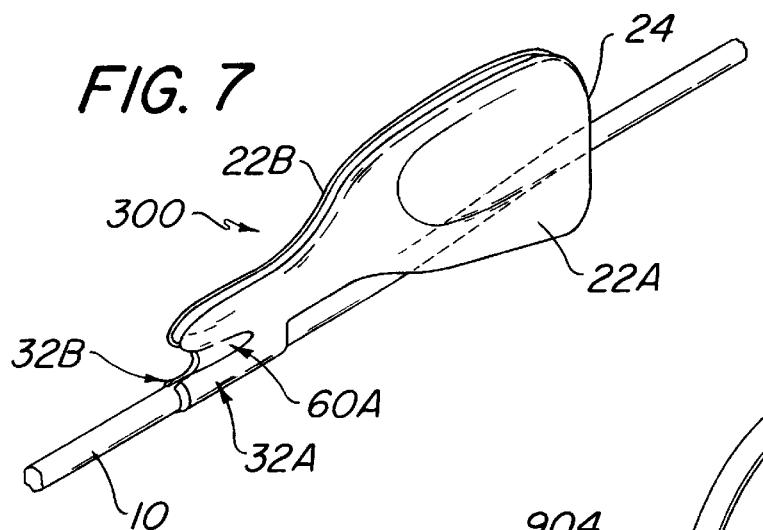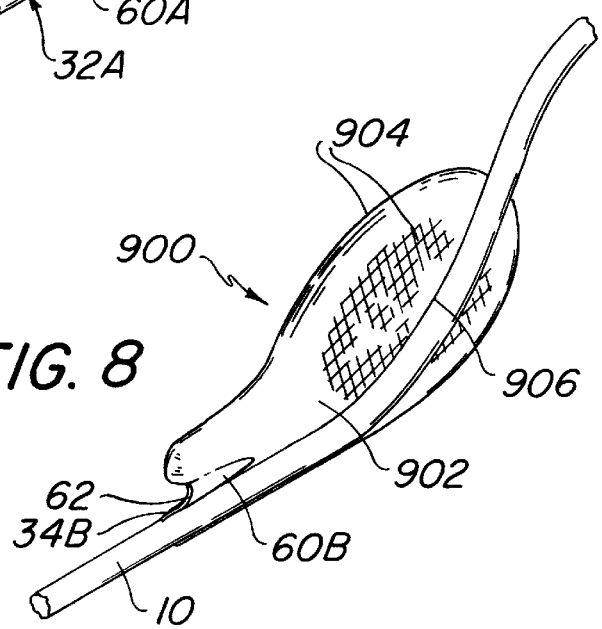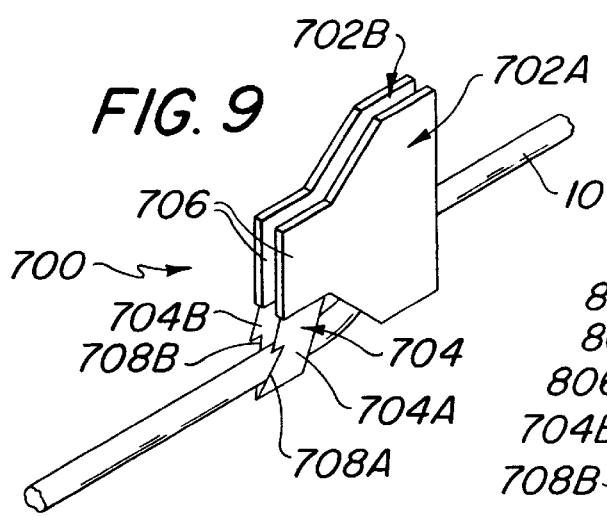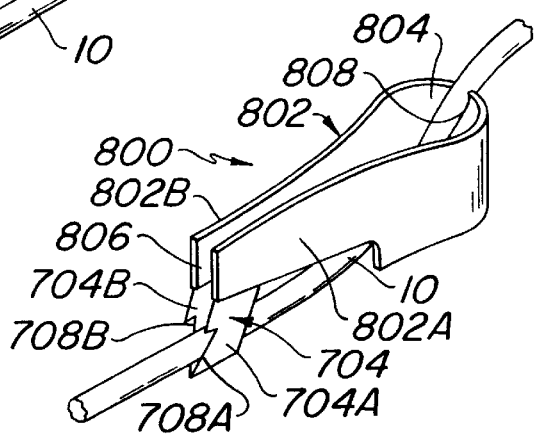

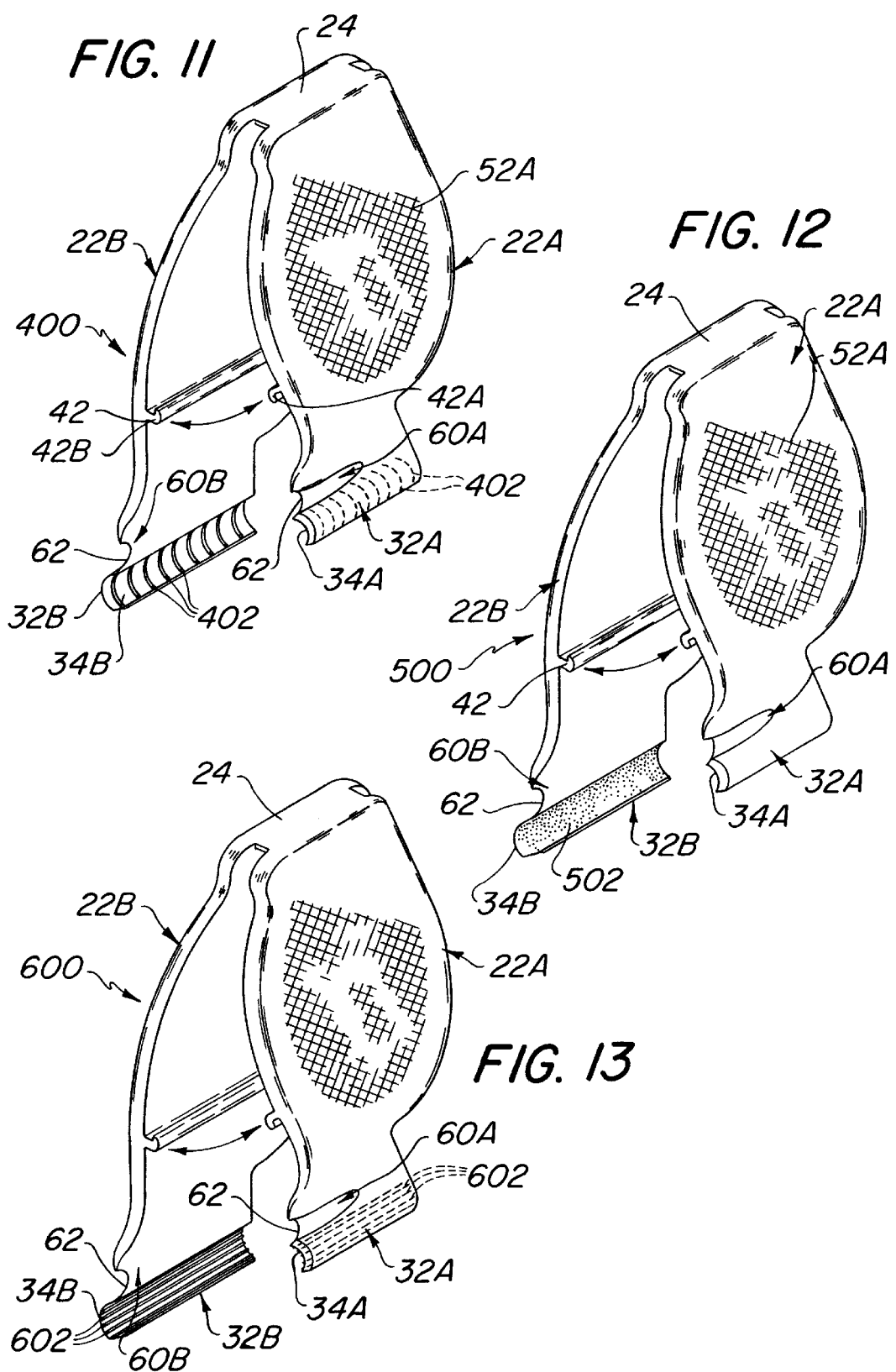

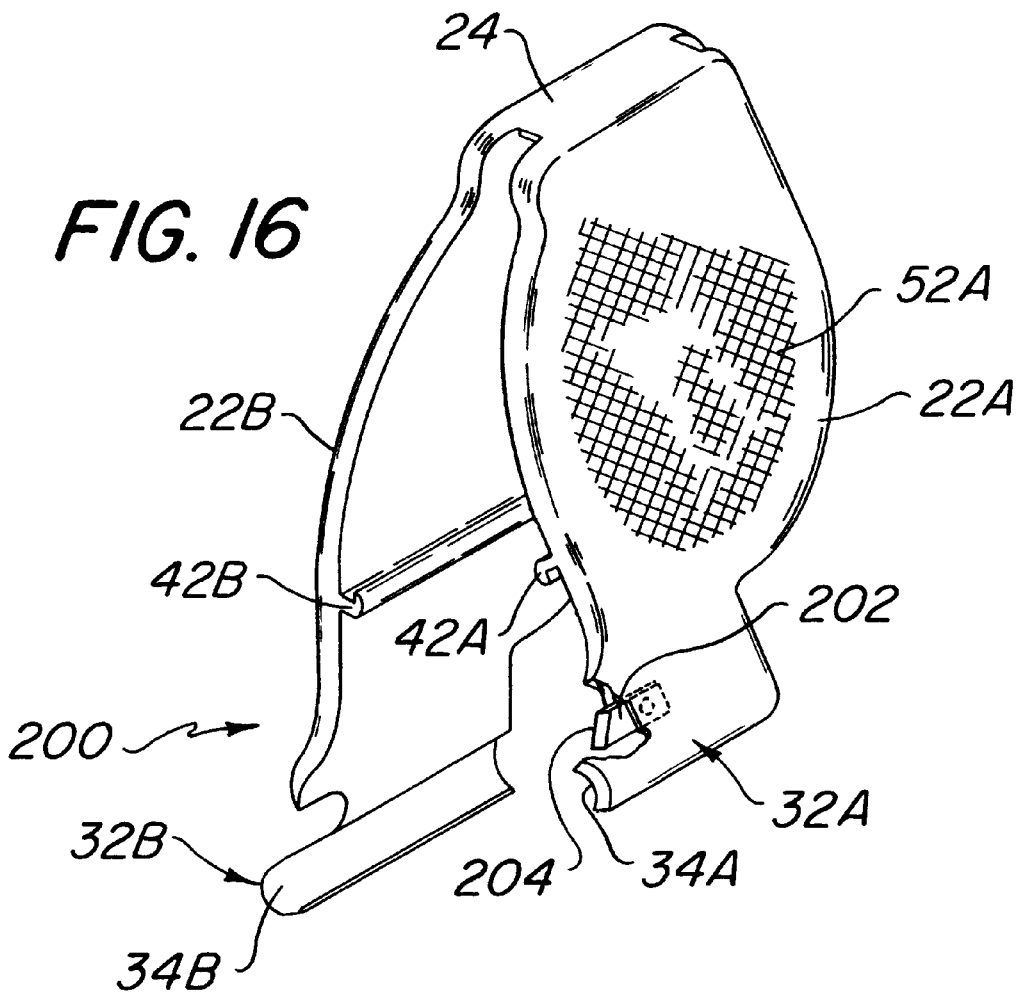

DEVICE AND METHOD FOR HOLDING AND MAINTAINING THE POSITION OF A MEDICAL DEVICE SUCH AS A CARDIAC PACING LEAD OR OTHER INTRAVASCULAR INSTRUMENT AND FOR FACILITATING REMOVAL OF A PEELABLE OR SPLITTABLE INTRODUCER SHEATH

BACKGROUND OF THE INVENTION

This invention relates generally to medical devices, and more particularly to devices and methods of use for removing an introducer sheath or other elongated tubular member which has been used to place a cardiac pacemaker (pacing) lead or other elongated intravascular instrument at a desired position within the body of a patient and without disturbing that pacing lead or instrument.

In U.S. Pat. No. 4,687,469 (Osypka) there is disclosed a hand-held slitter device for slitting a splittable introducer sheath used to place a cardiac pacing lead to permit the sheath to be removed without having to withdraw it over an end of a pacemaker lead.

In U.S. Pat. No. 5,713,867 (Morris) there is disclosed an introducer system including a kink-resistant sheath for use in placing a cardiac pacing lead. The sheath is constructed so that it can be readily split longitudinally utilizing a hand-held slitter device to permit the sheath to be removed without having to withdraw it over the proximal end of the pacemaker lead.

In current electrophysiology practice, the physician typically uses both hands to grasp and peel or split an introducer sheath to remove it from a cardiac pacing lead that has been positioned through the sheath to a desired location within the patient's body. A second person is sometimes used to hold the pacing lead in the desired position while the sheath is removed to ensure that the pacing lead is not displaced or moved. Alternatively, and more commonly, the physician holds the pacing lead with one hand, and withdraws the introducer sheath a short distance with the other hand. Then the physician grasps each half of the split peel-away hub and peels the sheath apart a short distance further. Once this is accomplished the physician again holds the pacing lead a little further up, and withdraws the introducer sheath a short distance further. This incremental series of motions is repeated several times until the introducer sheath is completely removed from the patient and the pacing lead, to minimize any displacement of the pacing lead.

As should be appreciated by those skilled in the art a primary concern of the physician during this repetitive procedure centers around the numerous manipulations necessary to remove the introducer from the pacing lead, and the significant potential for moving the freshly placed tip of the pacing lead, since some pacing leads exhibit a tendency to move out of position if the lead is pulled or otherwise disturbed.

Thus, need presently exists for a device for stabilizing or holding a cardiac pacing lead or any other elongated intravascular instrument at a desired position within a patient's body to facilitate the removal of a tearable or otherwise splittable introducer, without disturbing that pacing lead or other elongated intravascular instrument.

SUMMARY OF THE INVENTION

In accordance with one aspect of this invention a holding device is provided for use with an elongated flexible member, e.g., a cardiac pacing lead, and a tubular introducer member, e.g., a peelable or tearable introducer sheath or catheter. The tubular introducer member is arranged to be extended into the body of a living being, with the elongated flexible member arranged to extend through the tubular introducer member into the being's body for location at a desired position. The tubular introducer member is arranged to be withdrawn proximally from the being's body after the elongated flexible member is in the desired position. The elongated flexible member has a proximal portion that deters the tubular introducer member from being withdrawn out of the being's body while the elongated flexible member is in place extending through the tubular introducer member.

The holding device comprises a first portion, e.g., a "gripper" portion, and a second portion, e.g., a "splitter" portion. The first portion of the holding device is operable, e.g., includes at least one contoured engagement surface or jaw, to grasp a portion of the periphery of the elongated flexible member to hold the elongated flexible member at the desired position within the being's body. The second portion of the holding device is arranged to cause the tubular introducer member to separate longitudinally, e.g., the second portion includes a sharp edge portion for engaging the tubular introducer member to split the tubular introducer member longitudinally, when the tubular introducer member is withdrawn, e.g., pulled proximally with respect to the holding device, as the holding device is held in place gripping the elongated flexible member. Once it is separated, e.g., split, longitudinally, the tubular introducer member can be removed from the elongated flexible member leaving the elongated flexible member at the desired position within the being's body.

In accordance with another aspect of this invention a method is provided for holding an elongated flexible member, e.g., a cardiac pacing lead, in place extending into the body of a living being to a desired position through a tubular introducer member extending into the being's body, and for enabling the tubular introducer member to be withdrawn from the being's body when the elongated flexible member is held in place. The tubular introducer member includes a proximal portion. The elongated flexible member has a proximal portion that deters the tubular introducer member from being withdrawn out of the being's body while the elongated flexible member is in place extending through it.

The method comprises the steps of providing a holding device having a first portion and a second portion, longitudinally separating the proximal portion of the tubular introducer member to expose a portion of the periphery of the elongated flexible member, utilizing the first portion of the holding device to grip the exposed portion of the periphery of the elongated flexible member to hold the elongated flexible member at a desired position within the being's body, and withdrawing the tubular introducer member in the proximal direction to bring portions of it into engagement with the second portion of the holding device. This action causes the tubular introducer member to separate longitudinally along its entire length so that it can be removed from the being's body, leaving the elongated flexible member at the desired position within the being's body.

DESCRIPTION OF THE DRAWING

FIG. 7 is an isometric view of an alternative embodiment of a holding device constructed in accordance with this invention;

FIG. 8 is an isometric view of still another alternative embodiment of a holding device constructed in accordance with this invention;

FIG. 9 is an isometric view of still another alternative embodiment of a holding device constructed in accordance with this invention;

FIG. 10 is an isometric view of still another alternative embodiment of a holding device constructed in accordance with this invention;

FIG. 11 is an isometric view of yet another alternative embodiment of a holding device constructed in accordance with this invention, the device shown in FIG. 11 being similar in construction to that of FIG. 1B but including an alternative pacing lead "gripping" portion;

FIG. 12 is like that of FIG. 11, but showing another alternative pacing lead "gripping" portion;

FIG. 13 is like that of FIG. 11, but showing still another alternative pacing lead "gripping" portion;

FIG. 16 is an isometric view of yet another alternative embodiment of a holding device constructed in accordance with this invention, the device shown in FIG. 15 being similar in construction to that of FIG. 1B but including an alternative introducer sheath "splitting" portion.

DETAILED DESCRIPTION OF THE PREFERRED EMBODIMENT

Figure 3:
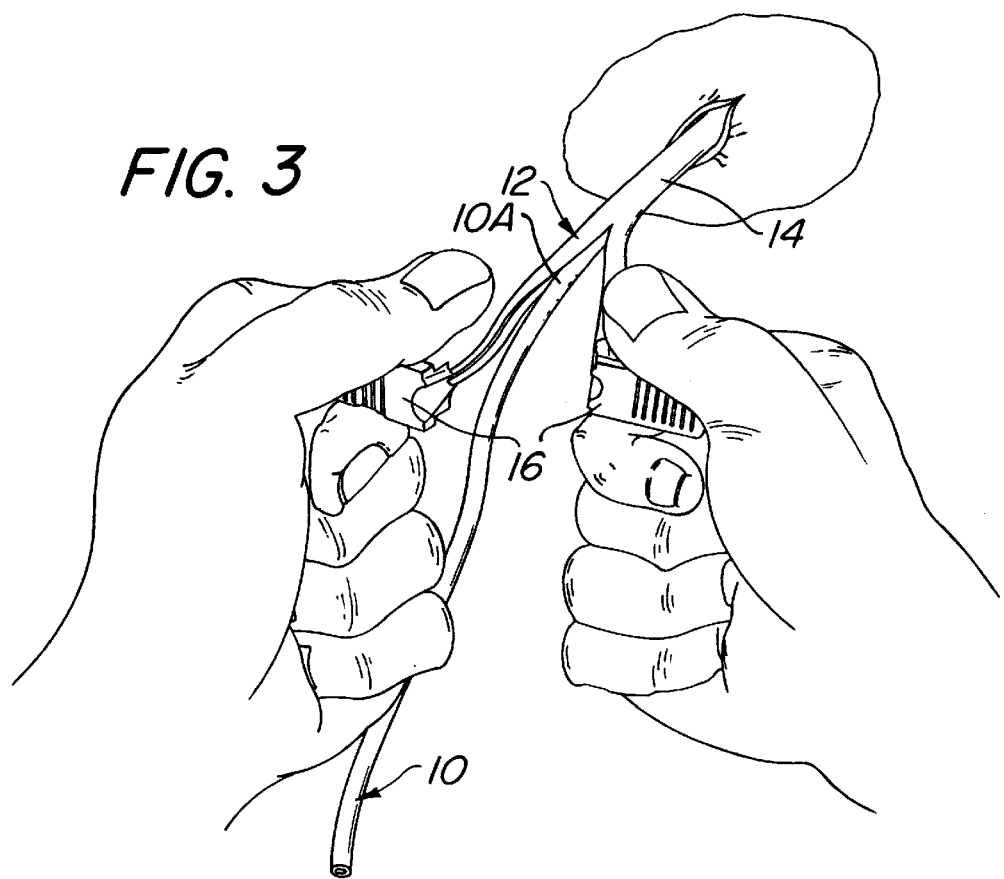
FIG. 3 is an illustration of an initial step in the process of removing a splittable or peelable introducer from the body of a patient without disturbing a cardiac pacing lead extending therethrough, the step being shown consisting of splitting the hub and contiguous portion of the introducer sheath to expose an underlying portion of the pacing lead.

Referring now to the various figures of the drawing wherein like reference characters refer to like parts, there is shown at 20 in FIG. 1 a holding device constructed in accordance with one embodiment of this invention for use with an elongated flexible member, e.g., a cardiac pacing lead 10 (FIG. 3) or other elongated flexible instrument or catheter, and a tubular introducer member 12 (FIG. 3). The introducer 12 is of any conventional type, e.g., a tubular instrument having peelable or tearable introducer sheath 14 and a splittable proximal hub 16. The cardiac pacing lead is also of any conventional construction. Thus, the details of the structure and operation of the cardiac pacing lead 10 and the introducer 12 will not be given herein. Suffice it to state that the pacing lead 10 is an elongated flexible member having a distal tip (not shown) arranged to be positioned intravascularly, via the introducer 12, at a desired cardiac location. The pacing lead 10 also includes an enlarged proximal end portion (not shown) which would tend to preclude the introducer from being withdrawn over the pacing lead to remove it from the patient's body after the pacing lead is in place. Thus, as noted above the introducer is splittable longitudinally, e.g., its sheath includes a least one weakened longitudinally extending line and its hub is either splittable or single-sided (connected to only one side of the sheath) and not splittable, so that the introducer sheath may be split longitudinally to remove it from the patient's body and the pacing lead.

As will be appreciated from the discussion to follow, the introducer 12 need not include a longitudinal weakened line for enabling it to be split longitudinally if the holding device of this invention to be used therewith includes a "splitter" portion suitable for cutting a longitudinally extending slit down the length of the introducer as it is being withdrawn from the patient's body. Thus, some of the embodiments of the holding device of this invention include a "splitter" portion in the form of a cutting element or knife blade suitable for that purpose.

Figure 1A:
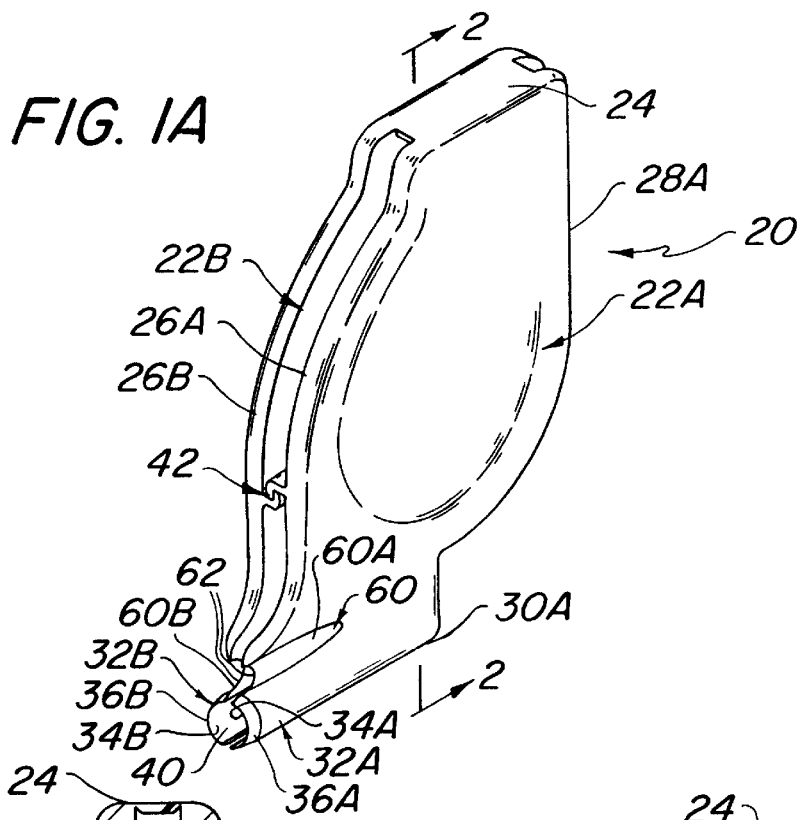
FIG. 1A is an isometric view of one embodiment of a holding device constructed in accordance with this invention.
Figure 1B:
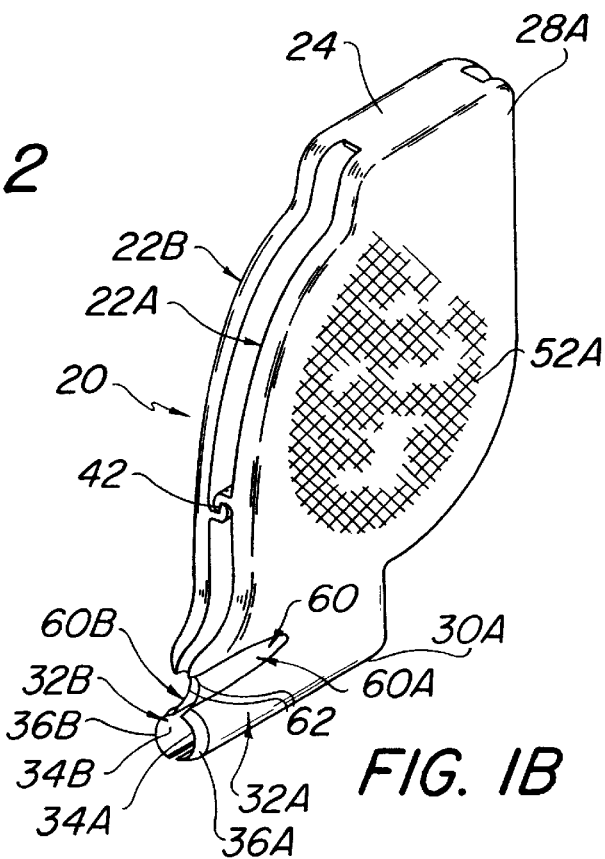
FIG. 1B is an isometric view of the embodiment device shown in FIG. 1, but having an alternative exterior surface for minimizing slippage in the hand of the user.

The holding device 20 shown in FIGS. 1A and 1B, as well as all of the other embodiments of this invention, enables the physician or other operator to place the pacing lead or other elongated flexible instrument at the desired location (e.g., on a portion of the heart) via the introducer and to stabilize or hold the pacing lead at that position with one hand, while enabling the physician/operator to pull or otherwise withdraw the sheath out of the patient's body in one natural motion with the other hand. This latter action is accomplished by the "splitter" portion of the device 20 automatically splitting the sheath as it is withdrawn past the device while the "gripper" portion of the device holds the pacing lead immobilized. Since the holding devices of this invention accomplish the dual action of stabilizing the pacing lead while facilitating the splitting and removal of the introducer sheath in one operation, the holding devices of this invention may sometimes be referred to hereinafter as a "tear-away assist stabilizer" devices.

The holding devices of FIGS. 1A and 1B are identical in structure and operation except that each includes a different type of contoured exterior surface to enable it to be readily and comfortably grasped between the thumb and forefinger of one hand of the physician/operator while being resistant to slippage. Thus, in the interest of brevity the common components or features of the device 20 shown in FIGS. 1A and 1B will be given the same reference numbers.

Figure 2:
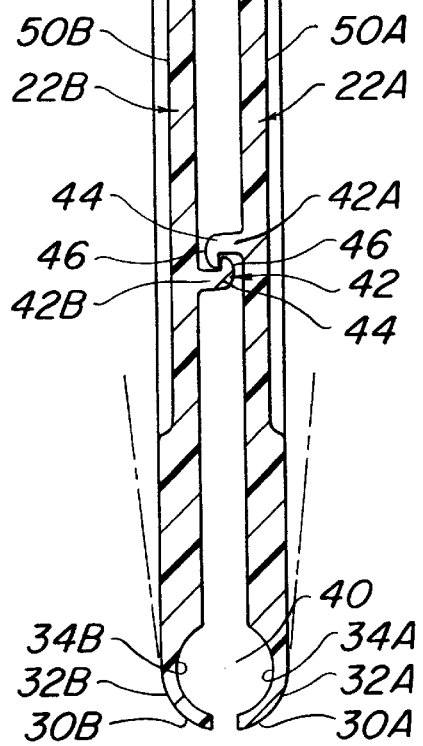
FIG. 2 is an enlarged sectional view taken along line 2—2 of FIG. 1.

The holding device 20 of FIGS. 1A and 1B is preferably molded as an integral unit of any suitable material, e.g., a plastic, and basically comprises a pair of generally planar sections handle 22A and 22B which in this exemplary embodiment are hingedly secured together via a living hinge 24 located at the top edge thereof. The handle sections may be connected together by some other joint or connection, not a hinge, if desired. For example, the handle sections can be fixedly connected together, but with those sections being flexible so that they can be flexed toward each other. Alternatively, the two handle sections can be separate members which are arranged to be assembled together either prior to or during use. In any case, the handle section 22A includes a front edge 26A, a rear edge 28A and a bottom portion 30A. The handle section 22B includes a front edge 26B, a rear edge 28B and a bottom portion 30B (FIG. 2). The two handle sections are arranged to be brought into a confronting parallel relationship with each other like shown in FIG. 2 by the user squeezing those two sections together between his/her thumb and forefinger of one hand. Alternatively, the device may be packaged in an assembled form wherein the handle sections confront each other, so that the user need not bring the two handle sections into that orientation. As will be understood from the discussion to follow once the device 20 is in the state wherein its handle sections are in their confronting relationship, the flexibility of either the hinge joint and/or the handle sections permits the user's finger pressure to press the two handle sections together to effect the gripping of the pacing lead.

As will be described later a connector assembly is provided in the device to hold the two handle sections in their confronting relationship against the natural bias provided by the living hinge 24 (or the natural bias provided by the inherent flexibility of the material(s) making up the handle sections). The connector assembly and the hinge or other element serving to connect the two handle sections together may, if desired, be integrated into one "joint" which can be fixed or not (depending upon the flexure of the confronting handle sections).

The bottom portion of the handle section 22A is in the form of an elongated arcuate wall 32A extending linearly along the bottom of section 22A, while the bottom portion of the handle section 22B is in the form of a similar elongated arcuate wall 32B extending linearly along the bottom of section 22B. The arcuate wall 32A includes an inner surface 34A whose radius is approximately that of the pacing lead, with the arc of that wall being slightly less than 180 degrees. The wall 32A also includes an inner surface 34B whose radius is approximately that of the pacing lead, with the arc of that wall also being slightly less than 180 degrees. The inner surfaces 34A and 34B form respective engagement surfaces for a pair of jaws (to be described hereinafter). Suffice it to state that the engagement surfaces of the jaws are arranged to be brought into engagement with the pacing lead (or other elongated tubular member to grip it).

It should be pointed out at this juncture that the shape, size and texture of the inner engagement surface of one or both of the arcuate walls 32A and 32B may be designed to permit one engagement surface radius to accommodate and fit a variety of sizes of pacing leads. Moreover, the shape of either or both of the jaw engagement surface need not be arcuate, but can be of other shapes to create a channel of any desirable shape, e.g., diamond shaped, octagonally shaped, etc., to receive and grip the pacing lead.

As mentioned above, the arcuate walls 32A and 32B form a pair of openable/closable jaws arranged to grasp a portion of the periphery of the pacing lead therebetween to secure the holding device to the pacing lead. Thus, the jaws 32A and 32B form the heretofore mentioned "gripping" portion of the holding device 20.

When the device's two handle sections 22A and 22B are brought into the heretofore mentioned confronting relationship the jaws 32A and 32B are opposed to each other and form an open tubular channel 40 between their respective inner surfaces 34A and 34B. The inner diameter of the channel 40, as best seen in FIG. 2, is slightly larger than the outer diameter of the pacing lead 10. Thus, as will be described later, when the two handle sections 22A and 22B are brought into their parallel confronting relationship with a portion of the periphery of the pacing lead between the jaws, the pacing lead will be surrounded by those jaws, but not tightly engaged by their inner surfaces 34A and 34B. The holding device 20 can then be slid longitudinally down the pacing lead 10, while the pacing lead is held stationary (e.g., by some other means or by the physician or some other person), until the holding device 20 is brought to the desired position on the pacing lead to grip the pacing lead and stabilize it. To accomplish that end, the physician/operator merely squeezes the two sections 22A and 22B together between his/her thumb and forefinger to cause the inner surfaces 34A and 34B of the jaws to tightly (frictionally) grasp the contiguous peripheral portion of the pacing lead.

The connector assembly for holding the handle sections 22A and 22B in their parallel confronting relationship can take various forms. In the embodiment shown in FIGS. 1A and 1B, that assembly is designated by the reference number 42 and basically comprises a pair of identical connectors 42A and 42B (FIG. 2). The connector 42A is in the form of an elongated rib upstanding from the inner surface of the handle section 22A, while the connector 42B is in the form of an elongated rib upstanding from the inner surface of the handle section 22B. Each rib includes a flanged free end 44. The rib 42A extends across the inner surface of the handle section 22A parallel to the longitudinal axis of the jaw 32A and to the longitudinal or pivot axis of the hinge 24, with its flange 44 facing downward. The rib 42B extends across the inner surface of the handle section 22B parallel to the longitudinal axis of the jaw 32B and to the longitudinal axis of the hinge 24, with its flange 44 facing upward. Each of the flanges includes a rounded outer surface 46. The ribs 42A and 42B are located on their respective handle sections so that when the handle sections are brought into their parallel confronting relationship the rounded outer surfaces of the flanges ride over each other and the flanges interlock, like shown in FIGS. 1–3, whereupon the handle sections are held in their parallel confronting relationship against the natural bias provided by the living hinge 24.

When the handle sections 22A and 22B are squeezed further together (as will be described later) to cause the jaws to grip the portion of the pacing lead in the channel 40, the flange 44 of the rib 42A rides along the inner surface of the rib 42B, while the flange 44 of the rib 42B rides along the inner surface of the rib 42A to generally maintain the parallelism of the handle sections, whereupon the inner surfaces of the jaws are brought generally diametrically into engagement with the periphery of the pacing lead in the channel 40. This action ensures that the pacing lead is gripped securely and is not skewed or otherwise displaced during the gripping action.

Figure 14:
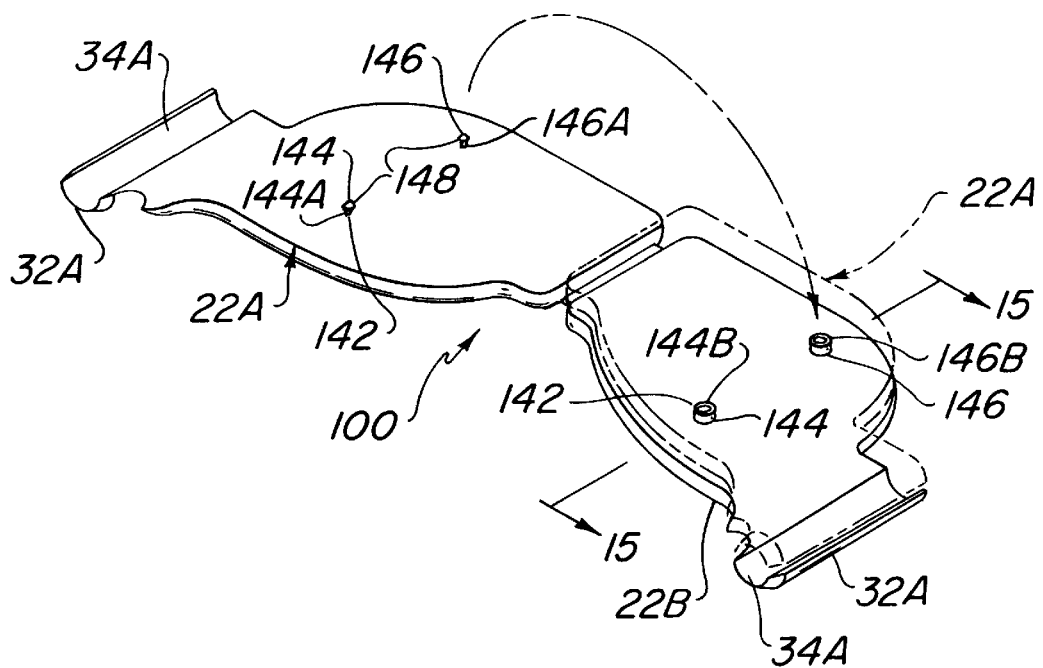
FIG. 14 is an isometric view of yet another alternative embodiment of a holding device constructed in accordance with this invention, the device shown in FIG. 14 being laid flat or open and being similar in construction to that of FIG. 1B, but including an alternative connector arrangement.
Figure 15:
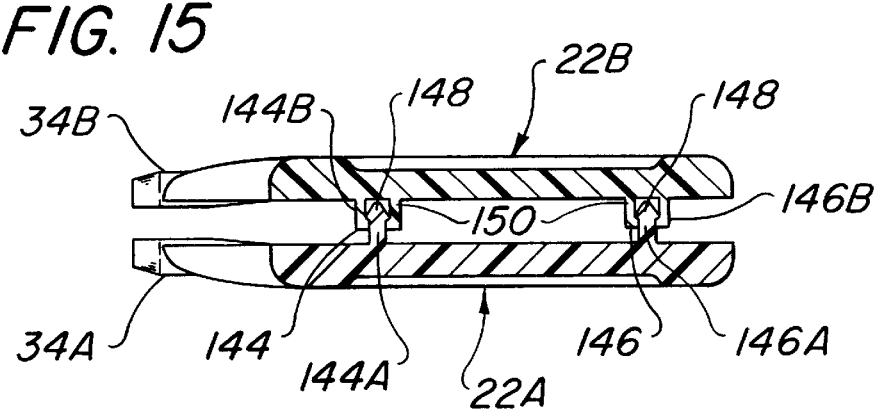
FIG. 15 is an enlarged sectional view taken along line 15—15 of FIG. 14.

In FIG. 14 there is shown a holding device 100 which is identical to the device 20, except for the use of an alternative connector assembly 142. Thus, in the interest of brevity the common components of the devices 20 and 100 will be given the same reference numbers and the details of their structure and operation will not be reiterated. The connector assembly 142 basically comprises a pair of connectors 144 and 146. The connector 144 comprises a cylindrical post 144A projecting upward from the inner surface of the handle section 22A and a cylindrical socket 144B projecting upward from the inner surface of the handle section 22B located opposite to the post 144A. The post 144A includes an enlarged tapering free end or head 148 (FIG. 15). The socket 144B includes a hollow cylindrical bore, whose entry is partially covered by an annular flange 150. The connector 146 comprises a cylindrical post 146A projecting upward from the inner surface of the handle section 22A and a cylindrical socket 146B projecting upward from the inner surface of the handle section 22B located opposite to the post 146A. The post 146A includes an enlarged tapering free end or head 148. The socket 146B includes a hollow cylindrical bore, whose entry is partially covered by an annular flange 150.

The enlarged head 148 of the post 144A is arranged to snap through the annular flange 150 into the bore in the socket 144B and the enlarged head 148 of the post 146A arranged to snap the annular flange 150 into the bore in the socket 146B when the two handle sections 22A and 22B are brought into their parallel confronting relationship like shown in FIG. 15, whereupon the handle sections are held in that relationship against the natural bias provided by the living hinge 24. When the handle sections 22A and 22B are squeezed further together, (as will be described later) to cause the jaws 32A and 32B to grip the portion of the pacing lead in the channel 40, the posts 144A and 146A slide slightly deeper into their respective sockets 144B and 146B to generally maintain the parallelism of the handle sections, whereupon the inner surfaces of the jaws are brought generally diametrically into engagement with the periphery of the pacing lead in the channel 40. This action ensures that the pacing lead is gripped securely and is not skewed or otherwise displaced during the gripping action.

As should be appreciated by those skilled in the art other connector arrangements can be utilized to maintain generally parallelism of the handle sections and to hold those sections together.

In order to facilitate the squeezing of the two handle sections 22A and 22B together, they each include a contoured outer surface portion. In the embodiment shown in FIG. 1A the contoured surface portion of the handle section 22A comprises a shallow recess 50A (FIG. 2) ergonomically shaped to comfortably accommodate the thumb or forefinger of the user of the device. The handle section 22B also includes a similar recess 50B. In the embodiment shown in FIG. 1B, the contoured outer surface portion of the handle section 22A comprises a knurled or otherwise textured planar surface area 52A, while the contoured outer surface portion of the handle section 22B comprises a similar knurled or otherwise textured planar surface area (not shown). Other surface textures, contours or coverings can be utilized to facilitate gripping and in the interest of user comfort.

As best seen in FIGS. 1A and 1B, the front or distal end of the arcuate walls 32A and 32B forming the gripping jaws of the device 20 is beveled at 36A and 36B, respectively. This feature facilitates the insertion of the gripping portion of the device within the gap produced when the hub 14 and contiguous portion of the introducer sheath 16 is split to receive the exposed portion of the pacing lead 10 as will be described later.

The details of the "splitting" portion of the tear-away stabilizer (holder) device 20 will now be described, again referring to FIGS. 1A and 1B. The splitting portion of the device 20 is designated by the reference number 60 and basically comprises a blade-like member forming a portion of the front edge of each of the handle sections. In particular, the front edge 26A of the handle section 22A immediately proximally and above the distal or free end of the jaw 32A is of a reduced thickness to form a fin-like member 60A. The fin member 60A has a relatively sharp curved leading edge 62 extending upward from the jaw 32A. In a similar manner, the front edge 26B of the handle section 22B immediately proximally and above the distal or free end of the jaw 32B is of a reduced thickness to form a fin-like member 60B which has a relatively sharp curved leading edge 62 extending upward from the jaw 32B. When the two handles sections are squeezed together to cause their respective jaws to tightly engage the pacing lead, the two fin-like members 60A and 60B are spaced very close to each other and effectively form a single splitter member arranged to split or otherwise separate the introducer sheath longitudinally along the sheath's weakened line when the sheath is withdrawn from the patient's body past those fins, as will be described in the following discussion.

Figure 4:
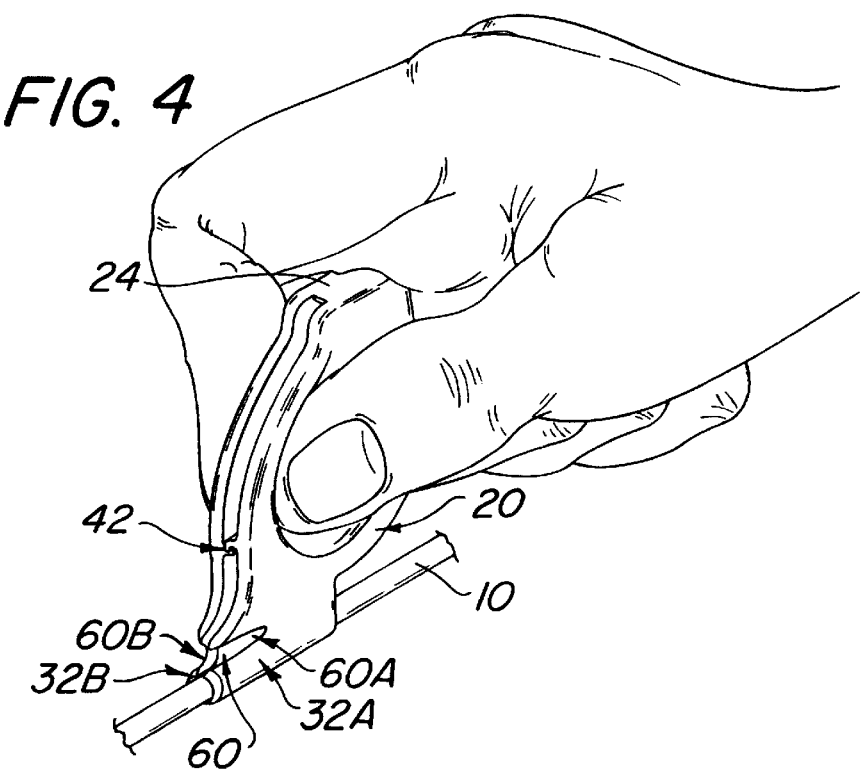
FIG. 4 is an illustration of a later step in the process of removing the splittable or peelable introducer sheath after the holding device of FIG. 1A has been grasped in one's hand and placed on a portion of the cardiac pacing lead.
Figure 5:
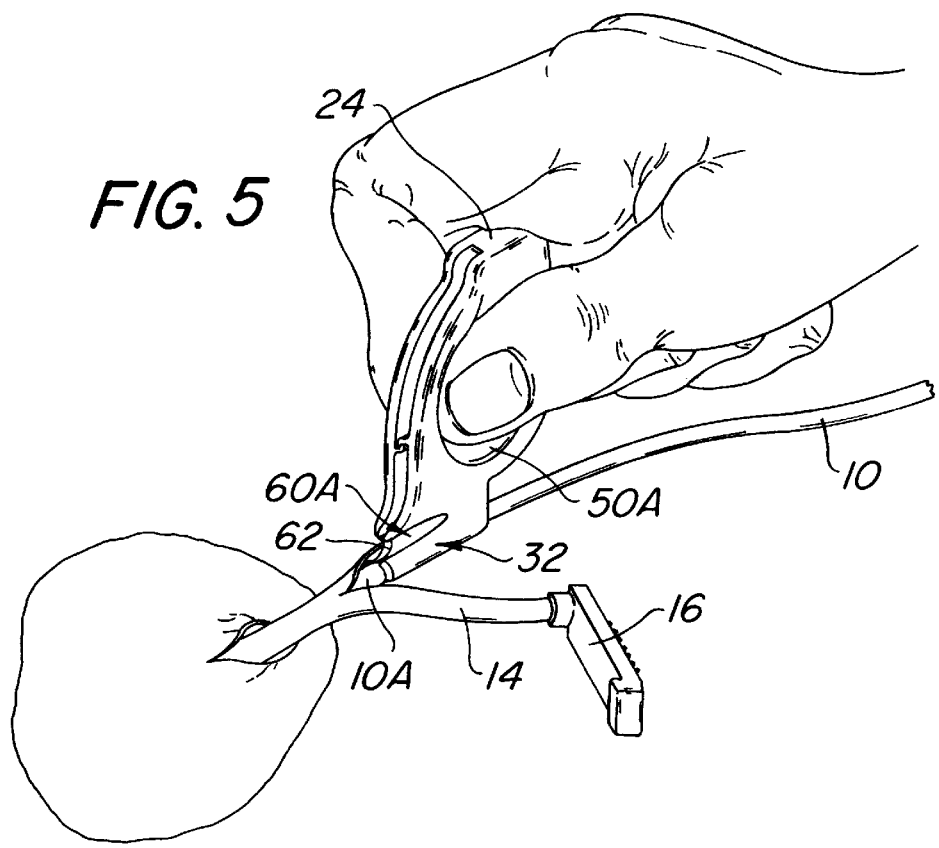
FIG. 5 is an illustration of a still later step in the process of removing the splittable or peelable introducer sheath by sliding the holding device with one hand along the pacing lead into the split hub of the introducer sheath so that the device's "gripping" portion receives the portion of the pacing lead exposed by the split sheath.
Figure 6:
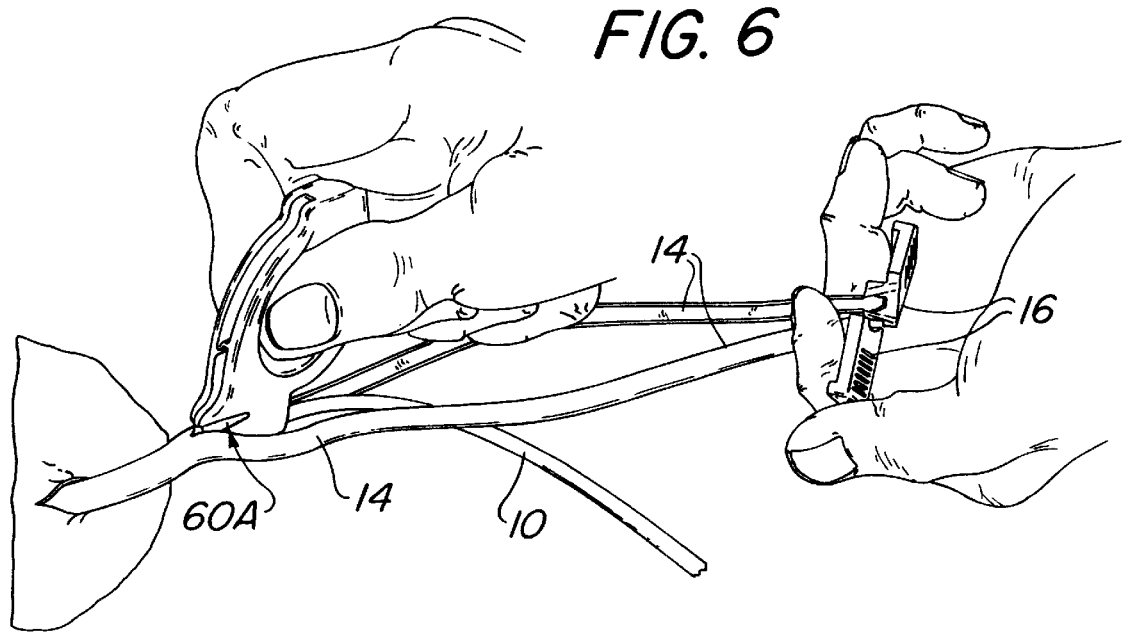
FIG. 6 is an illustration of a still later step in the process of removing the splittable or peelable introducer sheath by withdrawing the introducer from the patient's body in one motion with the other hand, while the one hand squeezes the holding device to cause the "gripping" portion to grasp the pacing lead and hold it in a stabilized, stationary position, so that the "splitter" portion of the holding device splits or otherwise longitudinally separates the sheath as it is withdrawn past the device.

Use of the device 20 will now be described in connection with one exemplary application and procedure, e.g., the placing of a cardiac pacing lead 10 at desired position within the body of a patient via the use of a peel-away or splittable introducer 12, as is commonly accomplished in electrophysiology. To that end, following the placement of the pacing lead 10 at its desired position within the body of the patient, the physician/operator first grasps the tear-away or splittable hub 14 of at the proximal end of the introducer 12 to split the hub 16 and the contiguous portion introducer sheath 14 in half longitudinally, as shown in FIG. 3. This action exposes a portion 10A of the cardiac pacing lead 10 previously within the confines of the introducer sheath 14. Then the physician/operator picks up the holding device 20 between his/her thumb and forefinger of one hand to bring the handle sections towards their parallel confronting relationship, with a portion of the pacing lead located between the open jaws. Further squeezing of the handle sections together brings the sections into their parallel confronting relationship, with the pacing lead located within the channel 40, as shown in FIG. 4. The physician/operator then slides the device 20 down the pacing lead (i.e., in the distal direction) until the device becomes wedged in the tear-away sheath 14 beyond (distally) of the two pieces of the now-split hub 14, i.e., into the exposed portion 10A of the pacing lead, as shown in FIG. 5. The physician/operator then grips and holds the two pieces of the split tear-away hub 16 in the other hand, while holding the device 20 in the one hand and squeezing its two handle sections 22A and 22B more closely together to cause the inner surfaces 34A and 34B of the confronting jaws 32A and 32B, respectively, to tightly clamp the periphery of the pacing lead therebetween. The frictional engagement of the device's jaws on the pacing lead while the device is held stationary in by the one hand of the physician/operator stabilizes the pacing lead and holds it in place. Then, while holding the device 20 in position secured to the pacing lead, the physician/operator uses his/her other hand to pull on the two pieces of the split hub 16 and the sheath 14 connected to the split hub as shown in FIG. 6 to withdraw the sheath out of the patient's body and towards the physician/operator. This action brings the weakened or splittable portions of the sheath 14 into engagement with the curved leading edges 62 of the closely spaced fin members 60A and 60B to split the sheath as the sheath 14 is pulled past them out of the patient's body.

As can be seen clearly in FIG. 2 the width of the portions of the opposed exterior surfaces of the device 20 that are aligned with the fin members 60A and 60B and extend above the centerline of the channel 40 is greater than the width of the portions of the opposed exterior surfaces of the arcuate walls 32A and 32B below that centerline. Thus, when the introducer sheath is split by the fins, it will tend to slide or fall off of the device 20 and away from the pacing lead. In order to enhance the tendency of the device to cause the sheath to fall or slide off of it when the sheath is split by the fins, the device 20 can be constructed so that the opposed portions of the exterior surface of the device along the section line 2—2 that are located above the channel's centerline flare outward from the arcuate walls 32A and 32B as shown by the phantom lines in FIG. 2.

Once the sheath 14 has been fully split (and it has been manually removed or has fallen or slid off of the device 20—as the case may be), the physician/operator can remove the device 20 from the pacing lead 10 by merely releasing his/her grip so that the device's jaws are freed from the pacing lead.

It should be pointed out at this juncture that while the device 20 described heretofore makes use of a splitter comprising a pair of closely spaced parallel fins 60A and 60B to split or separate the weakened line of the sheath 16 as it is brought into contact with those fins when the sheath is withdrawn out of the patient's body, other structure(s) designed to cause the weakened portion of the sheath to separate or split and to propagate the split down the length of the sheath may be used in lieu of such fins. Moreover, if desired, only one of the handle sections need include a splitter member, be it a fin or otherwise.

Where the introducer sheath does not include any weakened longitudinally extending line, e.g., a reinforced sheath, the "splitter" portion of a holding device constructed in accordance with this invention preferably comprises a cutting blade, knife or other element suitable to cut or sever the sheath longitudinally as it is drawn into engagement therewith. For example, in FIG. 16 there is shown an alternative embodiment of a holding device 200 constructed in accordance with this invention which incorporates such a cutting element. The device 200 is identical to the device 20 described with respect to FIG. 1B, except that its "splitter" does not comprise the heretofore identified fins 60A and 60B. Rather the device 200 comprises a "splitter" in the form of a single metal blade 202 fixedly mounted on the front edge of one of the handle sections, e.g., section 22A, immediately proximally and above the distal or free end of the associated jaw, e.g., jaw 32A. The blade has a sharp cutting edge 204 extending upward and at an acute proximally directed angle from the jaw 32A. If desired the other handle section may also include a similar cutter blade.

In FIG. 7 there is shown an alternative embodiment of a holding device 300 constructed in accordance with this invention. The device 300 is identical to the device 20 described heretofore except for its overall shape and the fact that its hinge 24 is located between the rear edges of the two handle sections 22A and 22B and the connector assembly comprising the flanged ribs (not shown) is oriented parallel to the longitudinal axis of the hinge.

In the embodiments of the devices shown in FIGS. 1A, 1B, 7, 14 and 16 the arcuate inner or gripping surfaces 34A and 34B of the jaws 32A and 32B, respectively, are smooth. If additional frictional engagement is desired to be provided by those surfaces to grip the periphery of the pacing lead, those surfaces may be textured or otherwise contoured to achieve such enhanced engagement. To that end there is shown in FIG. 11 an alternative embodiment of a holding device 400 constructed in accordance with this invention. The device 400 is identical to the device 20 described with respect to FIG. 1B, except that its jaws' arcuate engagement surfaces 34A and 34B each include a plurality of equidistantly spaced transversely extending ridges 402.

In FIG. 12 there is shown another alternative embodiment of a holding device 500 constructed in accordance with this invention. The device 500 is identical to the device 20 described with respect to FIG. 1B, except that its jaw's arcuate engagement surfaces 34A and 34B are each textured or roughened (e.g., like sandpaper), at 502.

In FIG. 13 there is shown still another alternative embodiment of a holding device 600 constructed in accordance with this invention. The device 600 is identical to the device 20 described with respect to FIG. 1B, except that its jaw's arcuate engagement surfaces 34A and 34B each include a plurality of equidistantly spaced longitudinally extending ridges 602.

It should be pointed out at this juncture that the shape, size and arrangement of the surface features, textures or contours of the jaw engagement surfaces as discussed above is merely exemplary of a myriad of different shapes, sizes and arrangements contemplated by this invention. For example, the surface features can include recesses, detents, irregularly spaced or receding height ridges or bumps. Moreover, as mentioned above the shape of the jaw engagement surfaces need not be arcuate, but can be other shapes to define channels of different cross sections, such as a diamond shape, an octagon shape, etc. Further still the shape of the engagement surfaces may be such that the resulting channel transitions from one cross sectional shape to another. The various sizes and shapes of the engagement surfaces may not only provide enhanced gripping action but may also enable a single size device to be used to grip various sizes of pacing leads or other elongated flexible members.

In FIG. 9 there is shown yet another alternative, and very simple and inexpensive, holding device 700 constructed in accordance with this invention. The holding device 700 is of a very simple construction and basically comprises a pair of planar handle sections 702A and 702B, connected together by a lower section 704. Each of the handle sections includes a distally projecting portion 706. The lower section is a very thin, generally V-shaped flexible web of any suitable plastic or metal and comprises a pair of legs 704A and 704B. The leg 704A is fixedly secured at its top end on the lowermost portion of the projecting portion 706 of the handle section 702A. The leg 704B is fixedly secured at its top end on the lowermost portion of the projecting portion 706 of the handle section 702B. The leading edge of the legs 704A and 704B include wedge-shaped notch 708A and 708B, respectively. The wedge shaped notches merge together at the apex of the V-shaped lower section and form the "splitter" portion of the holding device 700. The "gripper" portion of the holding device 700 is made up by the inner surfaces of the two handles sections 702A and 702B and the inner surfaces of the legs 704A and 704B of lower section, e.g., those surfaces effectively define the device's "gripping jaws."

Use of the device 700 is similar to that described heretofore, e.g., when the device is in place on the pacing lead the two handle sections are squeezed together. This action causes the pacing lead 10 to be tightly gripped between the "gripping jaws" (e.g., the inner surface of legs 704A and 704B and the inner surfaces of the handle sections 702A and 702B). The introducer 12 (not shown) can then be withdrawn out of the patient's body in the same manner as described earlier to cause the leading edge of the device's wedge shaped notches 708A and 708B to engage the weakened line portion of the introducer sheath 14 to split it longitudinally as the sheath is pull past the holding device.

In FIG. 10 there is shown yet another alternative, and very simple and inexpensive, holding device 800 constructed in accordance with this invention. The holding device 800 is similar to the holding device 700, except that the device 800 makes use of an integral U-shaped handle in lieu of the two separate handle sections 702A and 702B. In particular, the holding device 800 includes a U-shaped handle member 802 having planar handle sections 802A and 802B connected together by an integral bridging section 804. Each of the handle sections includes a distally projecting portion 806. Like the holding device 700, the "splitter" portion of the holding device 800 is made up by the wedge shaped notches of the V-shaped lower section 704. The "gripper" portion of the holder device 800 is in the form of a U-shaped recess or groove 808 in the upper edge of the bridging section 804 and into which a portion of the pacing lead is snugly fit. Moreover, when the device's two handle sections 802A and 802B are squeezed together the inner surface of the leg portions 704A and 704B of the lower sections 704 also tightly engage the pacing lead 10 to further grip it in the same manner as is accomplished by the use of the device 700. The use of the holding device 800 to effect the stabilization of the pacing lead 10 and the concomitant splitting and removal of the introducer 12 is the same as described above is similar to that of the holding device 700.

In FIG. 8 there is shown yet another alternative, simple and inexpensive, holding device 900 constructed in accordance with this invention. The holding device 900 basically comprises a handle 902 shaped somewhat like the handle section 22B described heretofore, but having a contoured gripping surface 904 on each side of it (although only one side can be seen in FIG. 8). Unlike the devices described heretofore which make use of an opposed pair of clamping jaws to grip the pacing lead, the device 900 includes only a single gripping portion or "jaw." That jaw is in the form of an arcuate recess 34B like that described earlier, which is located on the bottom edge of the handle 902. Disposed above the recess 34B on the forward edge of the handle 902 is the "splitter" portion of the device. The splitter portion is in the form of a single fin-like member 60B similar to that described earlier. The recess 34B merges into a rearwardly extending arcuate groove 906 into which a portion of the pacing lead 10 or other elongated flexible member is located.

Use of the holding device 900 is similar to use of the devices of FIGS. 1A, B, 7, 14 and 16, except that to secure the holding device 900 to the pacing lead 10 to stabilize the pacing lead the physician/operator may use his/her thumb or forefinger to hold the pacing lead tightly against the arcuate inner surface 34B as the sheath 14 is withdrawn out of the patient's body. The size and shape of the engagement surface 34B may be designed so that the pacing lead can snap-fit therein. In such an alternative embodiment the physician/operator need not use his/her thumb to hold the pacing lead in place on the device. The groove 906 also serves to hold the pacing lead in place, particularly since the groove 906 is curved. This feature alone may be sufficient to hold the pacing lead in place. The curvature of the groove 906 also serves to keep the pacing lead out of the way during the introducer sheath removal procedure. An arcuate groove 906 can be used with other embodiments of the invention for these purposes.

As should be appreciated from the foregoing discussion, the holding devices of the present invention are particularly suitable to facilitate the removal of peelable, tearable or otherwise longitudinally severable introducer sheaths or catheters, while ensuring that the position of another device, e.g., a cardiac pacing lead or other instrument, passing though the introducer/catheter is not changed. Moreover, the introducer removal procedure can be carried out by a single physician/operator, more rapidly than usual since the method can be performed in a single continuous, natural, motion. Thus, the subject invention provides a considerable advantage over current practice.

Moreover, in current practice, the splittable introducer hub and sheath must be completely split in half along diametrically opposed longitudinally extending lines. To accomplish that task, the introducer sheath typically includes a pair of diametrically opposed longitudinally extending weakened or score lines. The present invention permits splitting along only one line, and only half of the introducer hub, thereby potentially lowering the forces required to complete the introducer splitting and removal operation.

Since the subject invention enables the introducer to be split and withdrawn in a single fluid motion, while the pacing lead or other instrument is firmly and securely held in position, the potential for pacing lead displacement is minimized if not eliminated, and the introducer-removal task is accomplished more rapidly than heretofore possible.

Further still, since the device of this invention is simple in construction, inexpensive to make, is easy to use and enables one to remove an introducer in one quick natural motion without displacing the cardiac pacing lead it should provide a very cost effective modality for effecting placement and removal of cardiac pacing leads or other flexible instruments.

It should be noted that while various embodiments of the device shown and described herein have entailed the use of the device in a vertical orientation, some embodiments in some applications may be used in different orientations, depending upon the desires of the user.

Without further elaboration the foregoing will so fully illustrate my invention that others may, by applying current or future knowledge, adopt the same for use under various conditions of service.

I claim:

1. A holding device for use with an elongated flexible member and a tubular introducer member, the tubular introducer member being arranged to be extended into the body of a living being, with the elongated flexible member being arranged to be extended through the tubular introducer member into the being's body for location at a desired position, said holding device comprising:

(A) a first portion and a second portion, (B) said first portion of said holding device being operable to grip a portion of the periphery of the elongated flexible member to hold the elongated flexible member at the desired position within the being's body, said second portion of said holding device being arranged to cause the tubular introducer member to separate longitudinally when the tubular introducer member is pulled proximally with respect to said holding device as said holding device grips the elongated flexible member, whereupon the tubular introducer member can be removed from the elongated flexible member leaving the elongated flexible member at the desired position within the being's body.

2. The holding device of claim 1 wherein said device is hand-holdable unit.

3. The holding device of claim 1 wherein said first portion of said device comprises a concave groove adapted to receive a portion of the periphery of the elongated flexible member therein.

4. The holding device of claim 1 wherein said second portion of said device comprises a sharp edge.

5. The holding device of claim 4 wherein said sharp edge is formed of metal.

6. The holding device of claim 3 wherein said second portion of said device comprises a sharp edge.

7. The holding device of claim 1 wherein said first portion of said device comprises a pair of opposed jaws which are arranged to be brought into engagement with a portion of the periphery of the elongated flexible member to tightly hold the portion of the periphery of the elongated flexible member therebetween.

8. The holding device of claim 7 wherein said second portion of said device comprises a sharp edge, said sharp edge being located proximally adjacent said pair of jaws.

9. The holding device of claim 7 additionally comprising at least one releasably securable connector for holding said pair of jaws in a confronting relationship with each other.

10. The holding device of claim 7 wherein said holding device comprises a pair of sections movably connected to each other, and wherein one of said jaws is located on one of said sections and the other of said jaws is located on the other of said sections, said sections being movable into a confronting relationship wherein said pair of jaws form a channel therebetween for receipt of the portion of the periphery of the elongated flexible member.

11. The holding device of claim 10 additionally comprising at least one releasably securable connector for holding said pair of sections in said confronting relationship.

12. The holding device of claim 10 wherein said jaws are biased so that the width of said channel is slightly larger than the diameter of the pacing lead to enable the pacing lead and the device to be slid with respect to each other when the elongated flexible member is within said channel.

13. The holding device of claim 12 wherein said jaws are arranged to be moved against the bias into engagement with respective portions of the periphery of the elongated flexible member.

14. The holding device of claim 13 wherein said sections are arranged to be squeezed together to move said jaws into engagement with the elongated flexible member.

15. The holding device of claim 7 wherein each of said sections includes a surface portion arranged to be squeezed by a user of said device to bring said pair of sections into said confronting relationship.

16. The holding device of claim 15 wherein said surface portion is contoured.

17. The holding device of claim 15 wherein said surface portion includes a depression.

18. The holding device of claim 15 wherein said surface portion is textured.

19. The holding device of claim 7 wherein each of said jaws includes a recessed surface for engaging a portion of the periphery of the elongated flexible member.

20. The holding device of claim 19 wherein each of said recessed surfaces is arcuate.

21. The holding device of claim 19 wherein each of said recessed surfaces is contoured to enhance its ability to grip the portion of the periphery of the elongated flexible member.

22. The holding device of claim 21 wherein said contoured surface is a textured frictional surface.

23. The holding device of claim 21 wherein said contoured surface comprises a plurality of longitudinally extending ridges.

24. The holding device of claim 21 wherein said contoured surface comprises a plurality of transversely extending ridges.

25. The holding device of claim 7 wherein said holding device comprises a pair of sections movably connected to each other, each of said sections being a generally planar member having a distal edge portion, and wherein one of said jaws comprises an recess extending from said distal edge portion of one of said pair of sections, and the other of said jaws comprises recess extending from said distal edge portion of the other of said pair of sections, said sections being in, or movable into, a confronting relationship wherein said recess form a central channel for engaging the periphery of the elongated flexible member.

26. The holding device of claim 25 wherein each of said recesses comprises an arcuate wall, said arcuate walls forming a tubular member having a central channel for engaging the periphery of the elongated flexible member when said sections are moved in said confronting relationship.

27. The holding device of claim 26 wherein each of said arcuate walls includes a free distal edge, each of said free distal edges being beveled.

28. The holding device of claim 26 wherein at least one of said arcuate walls includes a contoured surface to grip at least a portion of the periphery of the elongated flexible member.

29. The holding device of claim 28 wherein said contoured surface comprises a textured frictional surface.

30. The holding device of claim 28 wherein said contoured surface comprises a plurality of longitudinally extending ridges.

31. The holding device of claim 28 wherein said contoured surface comprises a plurality of transversely extending ridges.

32. The holding device of claim 26 wherein said second portion of said device comprises a sharp edge.

33. The holding device of claim 32 wherein said sharp edge is located on said distal edge portion of one of said pair of sections proximally of said arcuate wall extending from said distal edge portion.

34. The holding device of claim 1 wherein holding device is molded of a plastic material.

35. The holding device of claim 32 wherein holding device is molded of a plastic material.

36. The holding device of claim 35 wherein said sharp edge is formed of metal.

37. The holding device of claim 1 wherein said first portion includes a recessed surface for engaging of a portion of the periphery of the elongated flexible member.

38. The holding device of claim 37 wherein said recess is arcuate.

39. The holding device of claim 37 wherein said recessed surface is contoured to enhance its ability to grip the portion of the periphery of the elongated flexible member.

40. The holding device of claim 39 wherein said contoured surface is a textured frictional surface.

41. The holding device of claim 39 wherein said contoured surface comprises a plurality of longitudinally extending ridges.

42. The holding device of claim 39 wherein said contoured surface comprises a plurality of transversely extending ridges.

43. A method of holding an elongated flexible member in place extending into the body of a living being to a desired position through a tubular introducer member extending into the being's body, and for enabling the tubular introducer member to be withdrawn from the being's body as the elongated flexible member is held in place, said method comprising the steps of:

(A) providing a holding device having a first portion and a second portion, (B) longitudinally separating the proximal portion of the tubular introducer member to expose a portion of the periphery of the elongated flexible member, (C) utilizing said first portion of said holding device to grip an exposed portion of the periphery of the elongated flexible member to hold the elongated flexible member at a desired position within the body of the being, (D) withdrawing the tubular introducer member in the proximal direction to bring portions of it into engagement with the second portion of the holding device to cause the tubular introducer member to separate longitudinally along its entire length so that it can be removed from the being's body, leaving the elongated flexible member at the desired position within the being's body.

44. The method of claim 43 wherein said first portion of said holding device grips the portion of the periphery of the elongated flexible member which is exposed by the separation of the proximal portion of the tubular introducer member.

45. The method of claim 43 comprising the step of pulling on said enlarged proximal portion of the tubular introducer member in the proximal direction to withdraw said tubular introducer member out of the being's body.

46. The method of claim 43 wherein said second portion of said holding device comprises a sharp edge to split said tubular introducer member as it is withdrawn in the proximal direction.

47. The method of claim 43 wherein said elongated flexible member comprises a cardiac pacing lead.

48. The method of claim 47 wherein said tubular introducer member comprises a peelable or tearable introducer sheath or catheter.

49. The method of claim 43 wherein said tubular introducer member comprises a peelable or tearable introducer sheath or catheter.

* * * * *